United States Patent
Wahl et al.

(10) Patent No.: US 8,580,095 B2
(45) Date of Patent: Nov. 12, 2013

(54) SENSOR ELEMENT HAVING IMPROVED THERMAL PROPERTIES FOR DETERMINING A GAS COMPONENT

(75) Inventors: Thomas Wahl, Pforzheim (DE); Philipp Spies, Magstadt (DE); Lothar Diehl, Gerlingen (DE); Ralf Liedtke, Stuttgart (DE)

(73) Assignee: Robert Bosch GmbH, Stuttgart (DE)

( * ) Notice: Subject to any disclaimer, the term of this patent is extended or adjusted under 35 U.S.C. 154(b) by 1229 days.

(21) Appl. No.: 12/295,143

(22) PCT Filed: Feb. 8, 2007

(86) PCT No.: PCT/EP2007/051216
§ 371 (c)(1),
(2), (4) Date: Mar. 19, 2009

(87) PCT Pub. No.: WO2007/110266
PCT Pub. Date: Oct. 4, 2007

(65) Prior Publication Data
US 2009/0308748 A1 Dec. 17, 2009

(30) Foreign Application Priority Data
Mar. 28, 2006 (DE) .......................... 10 2006 014 248

(51) Int. Cl.
*G01N 27/416* (2006.01)
(52) U.S. Cl.
USPC .......................................... 204/426; 204/424
(58) Field of Classification Search
USPC .................. 204/408, 421–429; 219/209
See application file for complete search history.

(56) References Cited

U.S. PATENT DOCUMENTS

| | | | |
|---|---|---|---|
| 4,282,080 A | 8/1981 | Mueller et al. | |
| 4,639,305 A | 1/1987 | Shibata et al. | |
| 5,895,591 A * | 4/1999 | Kojima et al. | 219/209 |
| 6,284,112 B1 * | 9/2001 | Kato et al. | 204/425 |
| 6,340,419 B1 | 1/2002 | Nakae et al. | |
| 6,861,939 B1 | 3/2005 | Bischof et al. | |
| 2002/0063059 A1 * | 5/2002 | Sugiyama et al. | 204/426 |
| 2003/0029861 A1 | 2/2003 | Renz et al. | |
| 2008/0035480 A1 * | 2/2008 | Cramer et al. | 204/424 |

FOREIGN PATENT DOCUMENTS

| | | |
|---|---|---|
| DE | 40 06 085 | 8/1991 |
| DE | 199 38 416 | 3/2000 |
| EP | 0 709 670 | 5/1996 |
| FR | 2 451 580 | 10/1980 |
| JP | 60-259951 | 12/1985 |
| JP | 2002-228626 | 8/2002 |
| WO | WO 01/40783 | 6/2001 |
| WO | WO 02/18925 | 3/2002 |
| WO | WO 2005/090958 | 9/2005 |

OTHER PUBLICATIONS

International Search Report, PCT/EP2007/051216, dated May 14, 2007.

* cited by examiner

*Primary Examiner* — Keith Hendricks
*Assistant Examiner* — Kourtney S Carlson
(74) *Attorney, Agent, or Firm* — Kenyon & Kenyon LLP

(57) ABSTRACT

A sensor element for determining a gas component in a measuring gas includes a first and a second electrode, a solid electrolyte situated between the electrodes, a heater having a heating element, and an insulation surrounding the heating element, wherein the heating element has a meander pattern having a first external heating area, a second external heating area, a first internal heating area, and a second internal heating area.

15 Claims, 3 Drawing Sheets

Fig. 2 (II-II)

SENSOR ELEMENT HAVING IMPROVED THERMAL PROPERTIES FOR DETERMINING A GAS COMPONENT

FIELD OF THE INVENTION

The present invention relates to a sensor element for determining a gas component in a measuring gas, which is used, for example, in a lambda sensor for determining an oxygen component in an exhaust gas of an internal combustion engine.

BACKGROUND INFORMATION

Certain sensor elements in lambda sensors are conventional. Sensors of this type are normally operated at temperatures between 750° C. and 800° C. To ensure the lowest possible emissions during combustion, the lambda sensor must be promptly available for operation after an engine start. This is achieved by using an electric heater which is integrated into the sensor element. When the sensor is switched on, the heater needs a certain time until the sensor is heated up to operating temperature. This time is also known as light-off time. The electric power introduced via the heater may result in high mechanical stresses in the sensor element during the very short heat-up process of approximately 4 s due to uneven temperature distribution. These high mechanical stresses may, however, result in failure of the sensor.

SUMMARY

Example embodiments of the sensor element according to the present invention provide a very short heat-up time, yet significantly reduced stresses occur in the sensor element. This is achieved in that the heating element has a meander pattern. This makes it possible to heat a relatively large surface of the sensor element rapidly and uniformly. The meander pattern includes a first and a second external heating area, as well as a first and a second internal heating area.

The heating areas are preferably located in one plane in the sensor element. The heating power is thus used according to the present invention efficiently for heating, a maximally uniform temperature distribution within the sensor element being nevertheless possible for reducing mechanical stresses.

The first external heating area and the first internal heating area are preferably connected by a first arc-shaped heating area. The first and the second internal heating areas are connected by a second arc-shaped heating area, and the second internal heating area and the second external heating area are connected by a third arc-shaped heating area.

Particularly preferably, the two external heating areas and the two internal heating areas are situated essentially parallel to each other. The two external heating areas and the two internal heating areas are also preferably designed as straight heating areas.

To make controlled and different heating of different sections of the sensor element possible, the heating element preferably has different cross sections over its heating length formed by the internal and the external heating areas. The heating power introduced may thus be introduced in a controlled manner into the desired areas as a function of the cross section. A cross section of the first and the second internal heating areas that is larger than a cross section of the first and the second external heating areas is preferred in particular.

The changing cross sections of the heating element are preferably achieved by different widths of the heating areas. A width of the first and the second internal heating areas is preferably greater than a width of the first and the second external heating areas.

The sensor element preferably has a very small thermal mass ($V \cdot p \cdot c_p$, where V=volume, p=density, $c_p$=spec. heat capacity) on the side of the heating element facing away from the electrodes. The thermal mass must be reduced mainly below the heating area. This is preferably accomplished by a heat-insulating area. For this purpose, the sensor element preferably includes a heat-insulating area, which is situated on a side of the heating element facing away from the electrodes of the sensor element. The heat-insulating area is situated such that the condition $e/(e+f+g)=0.2-0.45$ is met, e being a distance between the heater and the heat-insulating area, f being a thickness of the heat-insulating area, and g being a distance of the heat-insulating area to a bottom of the sensor element. Alternatively, the very small thermal mass on the side of the heating element facing away from the electrodes may be achieved by reducing the thickness and/or the density of the non-functional support foil of the heating element. Particularly preferred is not to have any support foil situated below the heating element, so that the gas mixture surrounding the sensor element may be used for heat insulating.

Furthermore, the sensor element preferably meets the condition $z/j=0.7$ to $0.95$, where z is the distance from the outer edge of the first external heating area to the outer edge of the second external heating area and j is an overall width of the sensor element.

According to another example embodiment, the sensor element meets the condition $y/z=0.05$ to $0.35$, where y is a distance between the first internal heating area and the second internal heating area of the heating element and z is the distance from the outer edge of the first external heating area to the outer edge of the second external heating area.

The heating element of the sensor element preferably meets the condition that a ratio of the cross section of the external heating areas to the internal heating areas is between 0.7 and 1.1.

The sensor element preferably also meets the condition $f/(e+f+g)>0.18$, where f is the thickness of the heat-insulating area and f is simultaneously also greater than or equal to 50 µm.

Furthermore preferably, the sensor element meets the condition $h/j=0.25$ to $0.75$, where h is a width of the heat-insulating area and j is an overall width of the sensor element.

According to a further example embodiment of the present invention, the sensor element includes a prechamber and a pump chamber, a width h of the prechamber being equal to a width of the pump chamber, and the condition $k/j=0.2$ to $0.5$ being met, where j is the overall width of the sensor element.

Furthermore preferably, the heat-insulating area has a length r and is situated at a distance m from a front face of the sensor element. The heating element is furthermore situated at a distance t from the front face and the external heating area of the heating element has a length u in the axial direction of the sensor element. The sensor element also meets the condition[s] $m/t=0.25$ to $0.4$ and $r/u=1.3$ to $1.45$.

The first prechamber and the pump chamber preferably have a distance a from a top of the sensor element, a thickness b and a distance c from the heater. The condition $c/(a+b)=0.1$ to $0.35$ is met.

Particularly preferably, the heat-insulating area is a cavity, which is filled with air in particular. This provides high heat insulation and, at the same time, a particularly simple manufacturability. It should, however, be pointed out that, as an alternative the heat-insulating area may also be a heat-insulating layer made of an insulating material.

To conduct heat into edge areas of the sensor element in a controlled manner, at least one lateral surface of the heat-insulating area has a convex or concave design.

Furthermore preferably, the heater and in particular the heating element of the heater is located in an approximately central area of the sensor element with respect to its sealing device.

An exemplary embodiment of the present invention is elucidated below with reference to the appended drawing.

DETAILED DESCRIPTION

A sensor element 1 according to an exemplary embodiment of the present invention is described below with reference to FIGS. 1 through 3.

Figure 1:
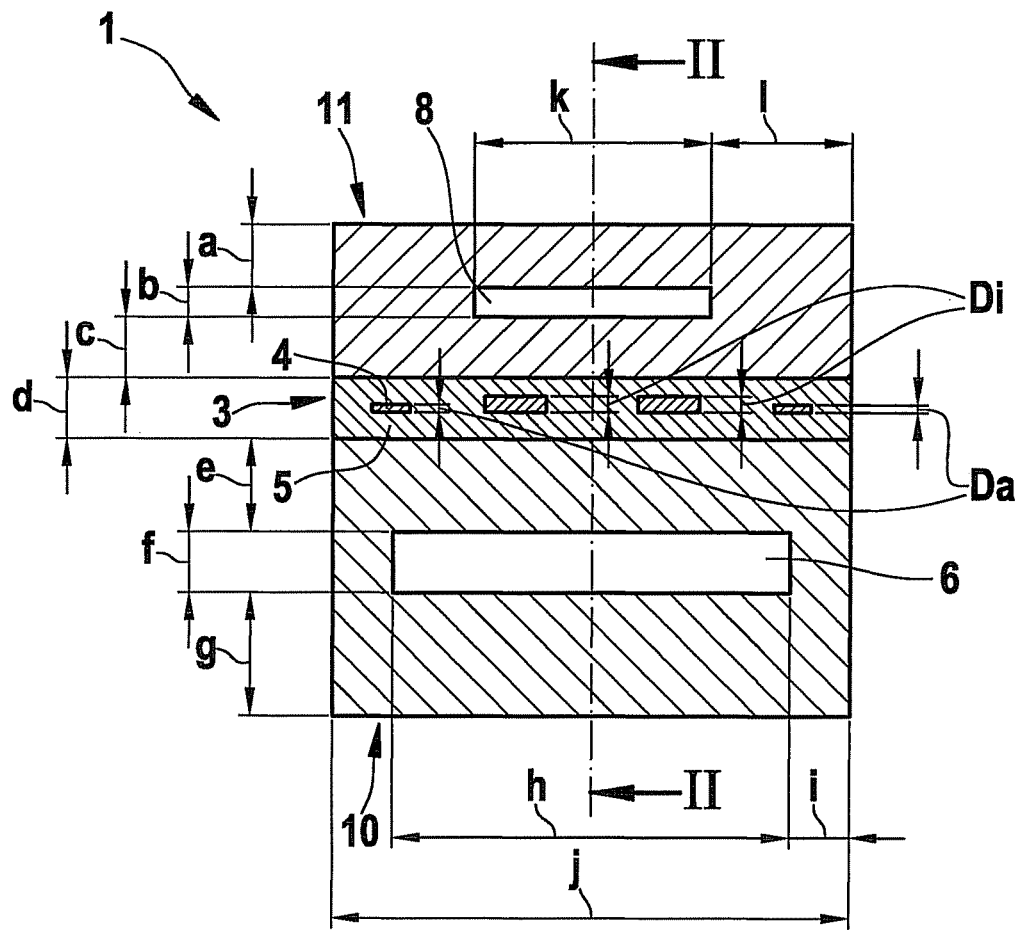
FIG. 1 shows a schematic sectional view of a sensor element according to an exemplary embodiment of the present invention.
Figure 2:
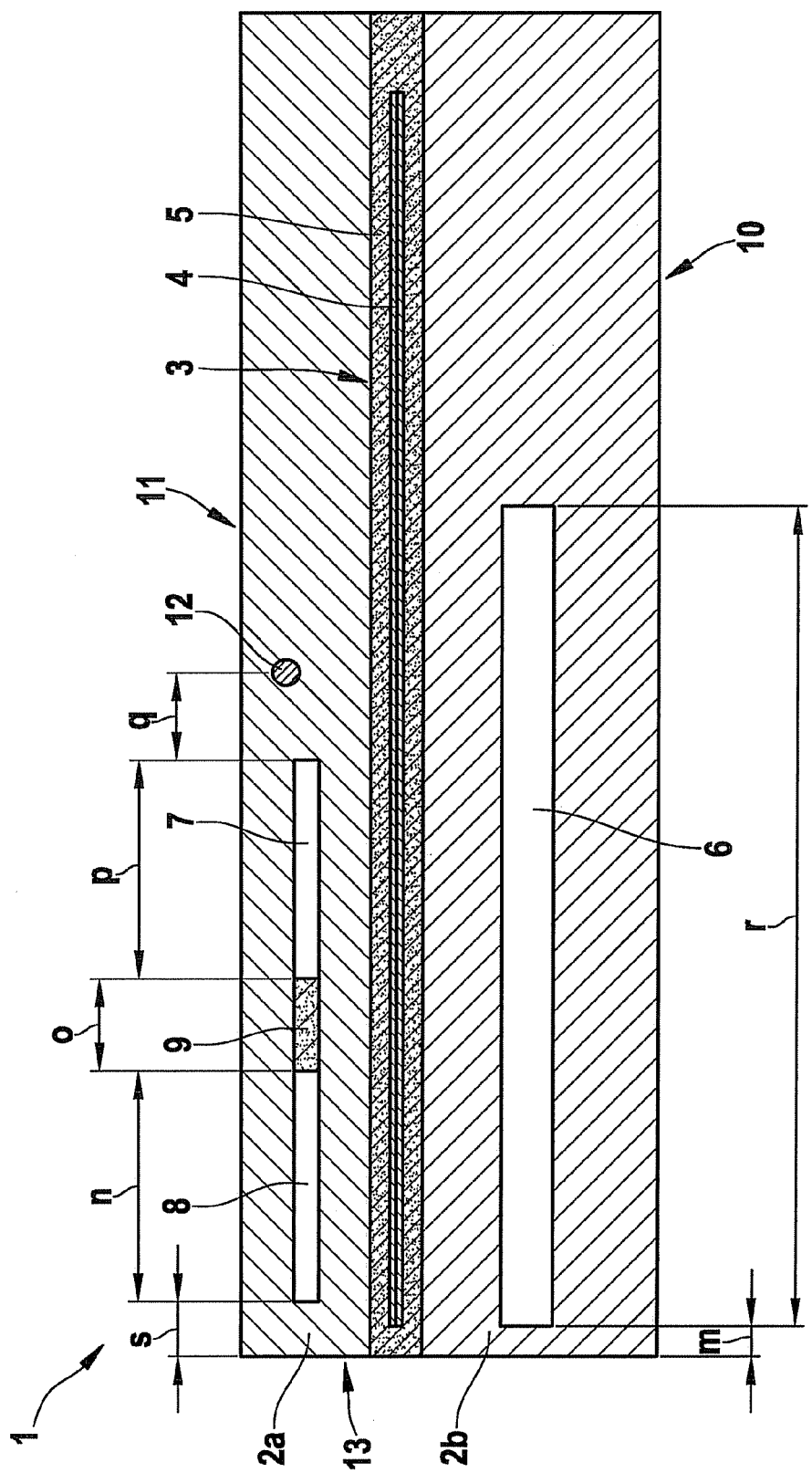
FIG. 2 shows a section along line II-II according to FIG. 1.

As is apparent from FIGS. 1 and 2 in particular, sensor element 1 includes a main body composed of a plurality of layers 2a, 2b made of a solid electrolyte material. The figures schematically show only two layers; however, multiple layers may be provided. Furthermore, the sensor element includes a heater 3, which includes a heating element 4, which is embedded in an insulation 5. Furthermore, sensor element 1 includes a prechamber 8 and a pump chamber 7, which are separated by a diffusion barrier 9. The diffusion barrier may have a linear design as in the exemplary embodiment, or also an annular design. Sensor element 1 schematically depicted in the figures is a lambda sensor for determining an oxygen content in the exhaust gas, and is designed as a broadband lambda sensor. Electrodes, preferably electrodes having a metallic component, in particular platinum, are situated in a conventional manner in pump chamber 7 and prechamber 8.

The thermal mass is furthermore to be reduced on a side of heater 2 facing away from pump chamber 7 and prechamber 8. This is achieved in the exemplary embodiment by providing a heat-insulating area 6 on the side facing away from pump chamber 7 and prechamber 8. As is apparent from FIGS. 1 and 3 in particular, heat-insulating area 6 has a rectangular design. Heat-insulating area 6 is filled with air and makes it possible to heat up the sensor element in the area of pump chamber 7 and prechamber 8 more rapidly because the heat dissipated downward by heater 3 only slowly reaches bottom 10 of the sensor element through heat-insulating area 6. More heat may thus be conducted to pump chamber 7 and prechamber 8.

It should be pointed out that the thermal mass may also be reduced by using a thin heater foil 2b. In that manner, less heat reaches the side facing away from the functional chambers and more heat is available for the functionally important area of the sensor element.

The temperature of the sensor element may be determined via thermoelectric device 12, for example, by measuring the resistance using thermoelectric device 12.

Figure 3:
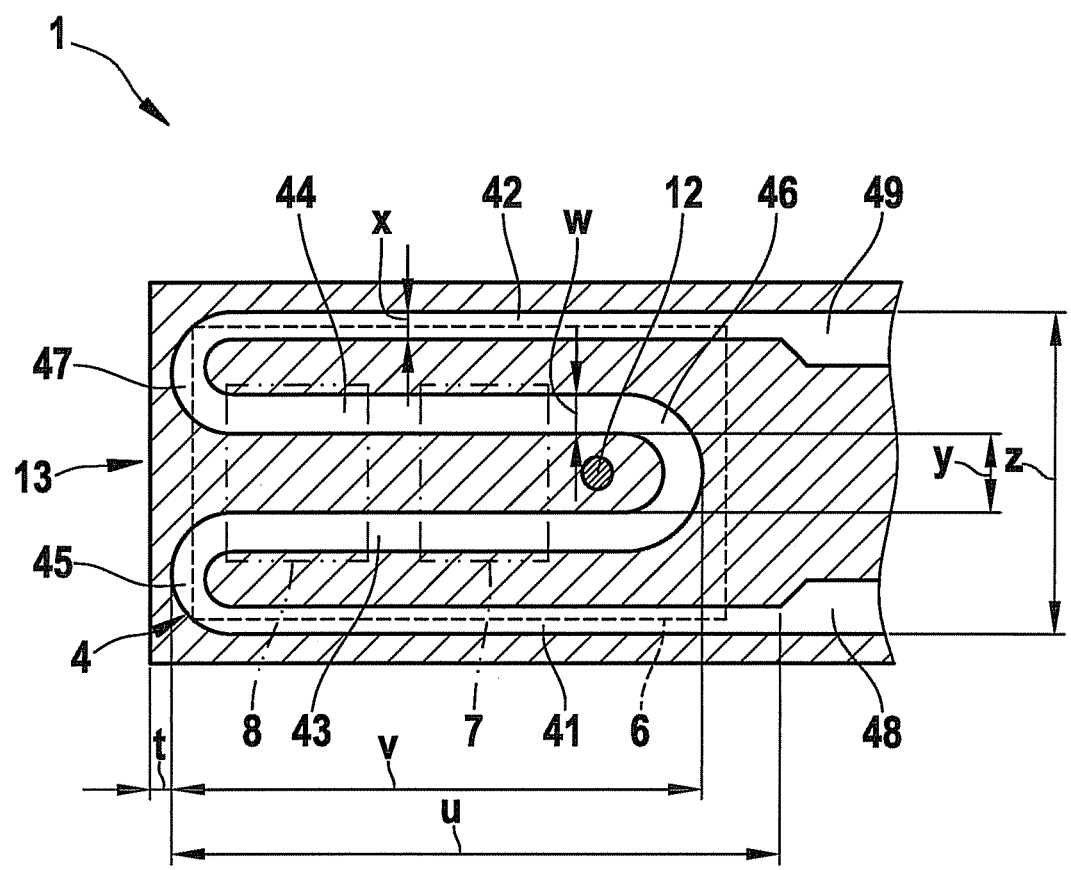
FIG. 3 shows a top view onto a longitudinal section in the area of the heater of the sensor element shown in FIGS. 1 and 2.

As FIG. 3 shows, heater 3 is designed such that it has a meander-patterned heating element 4. Meander-patterned heating element 4 is formed by a first external heating area 41, a second external heating area 42, a first internal heating area 43, and a second internal heating area 44. First external heating area 41 and first internal heating area 43 are connected via a first arc-shaped heating area 45. First internal heating area 43 and second internal heating area 44 are connected via a second arc-shaped heating area 46. Second internal heating area 44 and second external heating area 42 are connected via a third arc-shaped heating area 47. Heating element 4 is thus formed by three meandering heating loops. The terminal areas of heating element 4 depicted enlarged in FIG. 3 are labeled with reference numerals 48 and 49.

The distance between two adjacent external and internal heating areas is essentially the same. Furthermore, heating areas 41, 42, 43, 44 are essentially formed as straight segments and are situated parallel to each other.

As is further apparent from FIG. 3, a different cross-section $x^*D_a$ of the two external heating areas 41, 42 compared to cross-section $w^*D_i$ of the two internal heating areas 43, 44 is advantageous. This has the purpose of controlling the heat flow in such a way that the most uniform possible temperature distribution in the longitudinal and transverse directions of the sensor element is achieved. High temperature gradients are to be avoided because they result in high mechanical stresses and failure of the sensor element. Short light-off times are achievable only via uniform heating. If there are no restrictions regarding width z of the heating area, cross-section $x^*D_a$ of the two external heating areas 41, 42 is smaller than cross-section $w^*D_i$ of the two internal heating areas 43, 44. A widest possible heating area with respect to the overall width of the sensor element is advantageous in any case.

As is apparent from FIG. 3, the different cross sections are achieved via different widths and thicknesses of the heating areas. A width w of the two internal heating areas 43, 44 is greater than width x of the two external heating areas 41, 42, the two internal heating areas 43, 44 being situated below pump chamber 7 and prechamber 8. Because of the location of heat-insulating area 6 below heater 3, the most uniform possible temperature distribution is achieved. A very short light-off time of less than 3 seconds may thus be implemented.

As is further apparent from FIG. 1, the two external heating areas 41, 42 have a thickness Da, which is smaller than a thickness Di of the two internal heating areas 43, 44.

In the following, further design features of a sensor element 1, which improve a thermomechanical sturdiness of a lambda sensor in particular, are elucidated. Regarding heat-insulating area 6, which is filled with air, a width h, with respect to an overall width j of sensor element 1, is in a range of h/j=0.25 to 0.75. A distance e between heater 3 and heat-insulating area 6 has a considerable influence on the temperature distribution in the sensor element because this intermediary, heat-conducting layer contributes to a homogenization of the temperature field. However, a ratio of e/(e+f+g)=0.2 to 0.45 is to be met here, f being the thickness of heat-insulating area 6 and g being the thickness of the sensor element between a bottom 10 and heat-insulating area 6. As is further apparent from FIG. 2, a length r of heat-insulating area 6 and its distance m from a front face 13 of the sensor element are adapted to meander-patterned heating element 4. In particular, the ratios m/t=0.25 to 0.4 and r/u=1.3 to 1.45 are to be observed, t being a distance of heating element 4 from front face 13 and u being a length of external heating areas 41, 42 of heating element 4 in the longitudinal direction of the sensor element without terminal areas 48, 49 (see FIG. 3).

It should be further pointed out that the degree of heat insulation does not necessarily need to be homogeneous in heat-insulating area 6. The ratio between the heat conductivities of heating foil 2b and insulation 5 must be between 0.01 and 0.03. The degree of insulation is defined by the selection of the material and the thickness and possibly by providing conductive heat bridges. A thickness f of heat-insulating area 6 with respect to an overall thickness of heater 3 meets the condition $f/(e+f+g)>0.18$, f being at the same time greater than 50 µm.

Regarding the geometry of meander-patterned heating element 4, it should be further pointed out that a width z of heating element 4 located between the outer edge of first external heating area 41 and the outer edge of second external heating area 42 with respect to overall width j of the sensor element meets the condition $z/j=0.7$ to 0.95. A distance y between first internal heating area 43 and second internal heating area 44 with respect to overall width z of heating element 4 meets the condition $y/z=0.05$ to 0.35. A width k of the function chambers—pump chamber 7 and prechamber 8—with respect to overall width j of the sensor element meets the condition $k/j=0.2$ to 0.5.

It is furthermore advantageous for a temperature distribution if the external heating areas 41, 42 have exactly the same or more heating power than internal heating areas 43, 44. For this purpose, a cross section of external heating areas 41, 42 (x*Da) to a cross section of internal heating area[s] 43, 44 (w*Di) is in the range of $x*Da/w*Di=0.7$ to 1.1. It is to be further pointed out that the cross section may additionally vary over the length of each heating area 41, 42, 43, 44.

To improve the functional reliability of the sensor element, the condition $v/(s+n+o+p+q)=0.85$ to 1.2 is to be met for length v of the first and second internal heating areas 43, 44, s being a distance of prechamber 8 from front face 13, n being a length of prechamber 8 in the axial direction of the sensor element, o being a distance between prechamber 8 and pump chamber 7, p being a length of pump chamber 7 in the axial direction of the sensor element, and q being a distance of pump chamber 7 from thermoelectric device 12. For the length of the first and the second external heating areas 41, 42 the condition $u/(s+n+o+p+q)=0.95$ to 1.25 is to be met. Furthermore, the condition $t/(s+n)=0.45$ to 0.85 is to be met for the distance of heating element 4 from front face 13.

A minimum heating power is to be dissipated in the feed lines and terminal areas 48, 49 of heating element 4. Therefore, a ratio of 1 of the heating power of meander-patterned heating element 4 to the heating power of the feed line is to be achieved. A distance c of the function chambers—pump chamber 7 and prechamber 8—from heater 3 with respect to an overall thickness of the solid electrolyte layer (pump foil) must meet the condition $c/(a+b)=0.1$ to 0.35, a being a distance of the function chambers to a top 11 of the sensor element, b being a thickness of the function chambers, and c being a distance of the function chambers to heater 3 (see FIG. 1).

It should be pointed out that, as an alternative to the above-described exemplary embodiment, a sensor element may also be designed such that bottom layer 2b below heater 3 may be completely omitted. Heater 3 is then insulated downward by the gas mixture surrounding the sensor element.

The sensor element thus has a significantly shorter heating-up time until the operating temperature of the sensor element is reached, compared to certain conventional arrangements. Furthermore, the sensor element has substantially reduced mechanical stresses, so that it has a longer service life. The sensor element is used particularly preferably in connection with lambda sensors, in particular with broadband lambda sensors. The following table shows four examples, each of which has a meander-patterned heating element. Example 1 shows a sensor element according to a conventional arrangement without a heat-insulating area. Also in Example 4 no heat-insulating area 6 is provided.

As the table shows, Examples 1 and 4, however, have substantially longer heat-up times than Examples 2 and 3, each of which having a heat-insulating area 6. The last three lines of the table show the different heat-up times, the maximum main stresses, and the calculated probability of failure in absolute values. It results therefrom that the probability of failure of Example 2 is the lowest. As a comparison of Examples 2 and 3 shows, however, even providing a heat-insulating area 6 does not ensure that a minimum probability of failure is achieved. In particular when the maximum main stresses are very high, this has a negative effect on the probability of failure.

|  | Example 1 | Example 2 | Example 3 | Example 4 |
|---|---|---|---|---|
| h/j | — | 0.35 | 0.45 | — |
| e/(e + f + g) | — | 0.44 | 0.44 | — |
| m/t | — | 0.30 | 0.38 | — |
| r/u | — | 1.43 | 1.34 | — |
| f/(e + f + g) | — | 0.24 | 0.28 | — |
| z/j | 0.66 | 0.85 | 0.73 | 0.73 |
| y/z | 0.17 | 0.07 | 0.08 | 0.15 |
| k/j | 0.44 | 0.44 | 0.44 | 0.44 |
| $(x * D_a)/(w * D_i)$ | 1.00 | 0.90 | 1.07 | 0.88 |
| (v)/(s + n + o + p + q) | 1.07 | 0.89 | 1.00 | 0.99 |
| (u)/(s + n + o + p + q) | 1.20 | 0.96 | 1.02 | 1.04 |
| (t)/(s + n) | 0.47 | 0.84 | 0.67 | 0.67 |
| (c)/(a + b) | 0.21 | 0.31 | 0.31 | 0.31 |
| Heat-up time [s] | 4.9 | 3.01 | 2.91 | 3.17 |
| Maximum main stresses [MPa] | 189 | 179 | 244.7 | 191 |
| Calculated probability of failure [—] | $24.3 \cdot 10^{-6}$ | $16.3 \cdot 10^{-6}$ | $142.9 \cdot 10^{-6}$ | $27.9 \cdot 10^{-6}$ |

In Examples 2, 3 the light-off time is significantly reduced compared to Example 1 by a heat-insulating area. Example 3 shows an exemplary embodiment for an optimized design in which width z of the heating area relative to the overall width of the sensor element cannot be selected to be larger for reasons of basic manufacturing conditions. However, a design such as that in Example 2 is more convenient. The probability of failure may be significantly reduced by widening the heater. As is apparent from FIG. 3, under certain basic conditions, cross-section $x*D_a$ of the two external heating areas 41, 42 is to be selected to be greater than cross-section $w*D_i$ of the two internal heating areas 43, 44.

Example 4 shows an exemplary embodiment without a heat-insulating area, the thermal mass of the heater foil (2b) having been reduced here.

The last three lines of the table show the different heat-up times, the maximum main stresses, and a calculated probability of failure. It is apparent here that using the three optimized geometries (Examples 2, 3, 4) the light-off time is shortened from approximately 5 s from the related art of Example 1 to approximately 3 s. The probability of failure is not increased in the improved Examples 2, 3, and 4 compared to Example 1.

What is claimed is:

1. A sensor element for determining a gas component in a measuring gas, comprising:
    a first and a second electrode;
    a solid electrolyte situated between the electrodes;
    a heater having a heating element;
    an insulation surrounding the heating element; and
    a heat-insulating area arranged on a side of the heater facing away from the electrodes, the condition:

$h/j$=0.25 to 0.75 being met, h being a width of the heat-insulating area and j being an overall width of the sensor element;
    wherein the heating element has a meander pattern including a first external heating area, a second external heating area, a first internal heating area, and a second internal heating area;
    wherein the condition:

$e/(e+f+g)$=0.2 to 0.45 is met, e being a distance between the heater and the heat-insulating area, f being a thickness of the heat-insulating area, and g being a distance of the heat-insulating area to a bottom of the sensor element; and
    wherein the conditions:

$f/(e+f+g)$>0.18; and $f$≥50 μm are met, e being a distance between the heater and the heat-insulating area, f being a thickness of the heat-insulating area, and g being a distance of the heat-insulating area to a bottom of the sensor element.

2. The sensor element according to claim 1, further comprising a prechamber and a pump chamber, a width k of the prechamber being equal to a width of the pump chamber and the condition $k/j$=0.2 to 0.5 being met, where j is an overall width of the sensor element.

3. The sensor element according to claim 1, wherein the heat-insulating area has a length r in an axial direction of the sensor element and a distance m to a front face of the sensor element, and the heating element has a distance t to the front face and the heating element has a length u in the axial direction of the sensor element, and the conditions:

$m/t$=0.25 to 0.4 and $r/u$=1.3 to 1.45 are met.

4. The sensor element according to claim 1, wherein the heat-insulating area is a cavity, which is filled with air.

5. The sensor element according to claim 1, wherein the heat-insulating area includes at least one of (a) a convex and (b) a concave lateral surface.

6. The sensor element according to claim 1, wherein the heating element of the heater is situated approximately in a center with respect to an overall thickness of the sensor element.

7. The sensor element according to claim 1, wherein the first external heating area and the first internal heating area are connected via a first arc-shaped heating area, the first and the second internal heating areas are connected via a second arc-shaped heating area, and the second internal heating area and the second external heating area are connected via a third arc-shaped heating area.

8. The sensor element according to claim 1, wherein the internal and the external heating areas are substantially situated parallel to each other.

9. The sensor element according to claim 1, wherein the heating element has a variable cross section over its heating length.

10. The sensor element according to claim 9, wherein a cross-section of the first and the second internal heating areas is larger than a cross-section of the first and the second external heating areas.

11. The sensor element according to claim 9, wherein a width of the first and the second internal heating areas is greater than a width of the first and the second external heating areas.

12. The sensor element according to claim 9, wherein the heating element meets the condition:

$x*Da/w*Di$ =0.7 to 1, x being a width and Da being a thickness of the external heating areas and w being a width and Di being a thickness of the internal heating areas.

13. The sensor element according to claim 1, wherein the condition:

$z/j$=0.7 to 0.95 is met, where z is a distance from an outer edge of the first external heating area to the outer edge of the second external heating area and j is an overall width of the sensor element.

14. The sensor element according to claim 1, wherein the condition:

$y/z$=0.05 to 0.35 is met, where y is a distance between the first internal heating area and the second internal heating area and z is a distance between an outer edge of the first external heating area and an outer edge of the second external heating area.

15. A sensor element for determining a gas component in a measuring gas, comprising:
    a first and a second electrode;
    a solid electrolyte situated between the electrodes;
    a heater having a heating element;
    an insulation surrounding the heating element; and
    a heat-insulating area arranged on a side of the heater facing away from the electrodes, the condition:

$h/j$=0.25 to 0.75 being met, h being a width of the heat-insulating area and j being an overall width of the sensor element;
    wherein the heating element has a meander pattern including a first external heating area, a second external heating area, a first internal heating area, and a second internal heating area; and further comprising a prechamber and a pump chamber, the prechamber and the pump chamber having a distance a from a top of the sensor element, a thickness b and a distance c from the heater, and the condition:

$$c/(a+b)=0.1 \text{ to } 0.35$$

is met.

* * * * *

UNITED STATES PATENT AND TRADEMARK OFFICE
CERTIFICATE OF CORRECTION

PATENT NO.         : 8,580,095 B2
APPLICATION NO.    : 12/295143
DATED              : November 12, 2013
INVENTOR(S)        : Wahl et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1401 days.

Signed and Sealed this
Twenty-second Day of September, 2015

Michelle K. Lee
*Director of the United States Patent and Trademark Office*